United States Patent [19]

Abu-Shaaban

[11] Patent Number: 5,576,001
[45] Date of Patent: Nov. 19, 1996

[54] COMPOSITION FOR THE TREATMENT OF DIARRHEA, ITS USE AND ITS PREPARATION

[76] Inventor: Medhat Abu-Shaaban, 8529 Huntspring Dr., Lutherville, Md. 21093

[21] Appl. No.: 392,422

[22] Filed: Feb. 22, 1995

[51] Int. Cl.$^6$ .................................................. A61K 35/78
[52] U.S. Cl. ........................................ 424/195.1; 514/868
[58] Field of Search ........................ 424/195.1; 514/868

[56] References Cited

U.S. PATENT DOCUMENTS

| | | | |
|---|---|---|---|
| 4,950,140 | 8/1990 | Pflaumer et al. | 424/439 |
| 5,013,576 | 5/1991 | Nakazawa et al. | 426/640 |
| 5,132,113 | 7/1992 | Luca | 424/195.1 |

FOREIGN PATENT DOCUMENTS

| | | | |
|---|---|---|---|
| 5-286863 | 11/1993 | Japan | A61K 35/78 |

*Primary Examiner*—John W. Rollins
*Attorney, Agent, or Firm*—Lowe, Price, LeBlanc & Becker

[57] ABSTRACT

A composition for treating diarrhea comprises carrots, rice, bananas and glucose in powdered form, the carrots and rice having been cooked and dried prior to being ground to a powder. The composition may also contain one or more of powdered pineapple, apples, soybeans and maltodextrin. An effective amount of the composition is administered to a patient, such as an infant, to treat and alleviate diarrhea.

33 Claims, No Drawings

COMPOSITION FOR THE TREATMENT OF DIARRHEA, ITS USE AND ITS PREPARATION

BACKGROUND OF THE INVENTION

This invention relates to a composition for treating diarrhea, as well as to the use and to the preparation of said composition. Diarrhea is a widespread and recurring ailment that attacks adults, children, infants and warm-blooded animals throughout the world. It has been estimated that in the United States, 16.5 million children under the age of five years experience 21–37 million episodes of diarrhea each year, 10% of said episodes leading to a physician's visit. Over 200 thousand of the children are hospitalized and 325 to 425 of the children die, most of them infants under one year of age. On a worldwide basis, next to respiratory infections, diarrheal diseases are the leading cause of death among children under five years of age. Thus, it is evident that control of this condition deserves the attention of the medical and veterinary communities and is in need of an effective, low-cost, easily administrable therapeutic agent.

The proper relationship of nutrients, wastes, electrolytes, and water through the intestines depends on an appropriate balance of absorption and secretion of water and electrolytes by the intestinal epithelium. However, there are many forces that interfere with the normal functioning of the body, leading to diarrhea. These forces may involve infections, chemicals or radiation, for example, and may reflect the condition of the immune system, such as in HIV syndrome. The function of the anti-diarrheal agent generally is not to attack the cause of the condition, but to relieve the symptoms and discomfort associated with said condition.

The organisms responsible for diarrhea include those that cause amebiasis, cholera, infectious colitis, and bacteremia (particularly from Salmonella), in addition to the specific organisms, enterotoxigenic and invasive *Escherichia coli, Giardia lamblia, Isospora belli,* Shigella, *Strongyloides stercoralis,* and essentially all organisms for which there is effective antimicrobial therapy causing diarrhea in immuno-compromised hosts.

Other organisms guilty of producing diarrhea encompass viruses, such as cytomegalovirus, enteric adenovirus, picornavirus and rotavirus. Also, various parasites may be responsible for the condition. Included in this group, in addition to those already mentioned, are *Entamoeba histolytica, cryptosporidium* and Microsporidia species.

Some of the chemical agents causing diarrhea are adrenergic neuron blocking agents, such as reserpine and guanethidine; antimicrobials, such as sulfonamides, tetracyclines and most broad-spectrum agents; bile acids, carcinoid tumor secretions, e.g., 5-hydroxytryptamine and vasoactive intestinal peptide; cholinergic agonists and cholinesterase inhibitors; fatty acids; osmotic laxatives, such as sorbitol and saline cathartics; prokinetic agents, such as metoclopramide and domperidone; prostaglandins; quinidine; and stimulant laxatives.

Notwithstanding the above, in an article in *Pediatric Anals* 23:523–524 (October 1994), Dr. Robert A. Hoekelman, cautions that:

Non-antimicrobial medications should not be used for the treatment of diarrhea in infants and children because they provide no benefit and may worsen the diarrhea by slowing intestinal mobility and thereby the expulsion of organisms and toxins responsible for the diarrhea, and by preventing absorption and secretion from the intestinal wall. Some drugs that slow intestinal motility such as diphenoxylate hydrochloride-atropine sulfate and loperamide hydrochloride also may cause respiratory depression, coma, and death.

PRIOR ART

Among the many cures described for diarrhea is that claimed in U.S. Pat. No. 115,517, involving a composition containing opium, sugar, nutmeg and brandy. In U.S. Pat. No. 133,213, a similar composition is claimed consisting of white oak bark, cinnamon, cloves, dandelion root and brandy. While the first two patents were issued in the last century, more recent treatment of diarrhea involves the administration of an aqueous extract of oatmeal, as claimed in U.S. Pat. No. 4,765,981, issued in 1988. On the other hand, in U.S. Pat. No. 4,261,981, the patentee claims a method for preparing a composition from ragweed leaves, said composition being useful for treating diarrhea.

Even more recently, two patents, U.S. Pat. No. 5,149,541 and U.S. Pat. No. 5,234,916, assigned to the Proctor and Gamble Company, are concerned with treating diarrhea with a psyllium husk-containing drink mix composition and a divalent cation salt of a strong inorganic acid selected from magnesium sulfate, calcium sulfate, calcium chloride, zinc sulfate and/or zinc chloride and a carrier material therefor. In U.S. Pat. No. 5,149,541, the same type drink mix product is claimed, although the particular particle size distribution is also recited. Even more recently, U.S. Pat. No. 5,330,755, issued Jul. 19, 1994, a patent assigned to Nestec S. A., contains claims directed to a process for producing a carob product by treating ground-desugared carob pods with super-heated steam to pasteurize and dry the carob. The method for treating diarrhea by administering to a patient particulated carob pod having water-insoluble tannins is claimed in the assignee's earlier U.S. Pat. No. 5,043,160.

The failure of the foregoing therapeutic agents to be presently recognizable testifies to their ineffectiveness in controlling diarrhea. However, several products are currently popular in the United States for treating this ailment. These products include Imodium® (loperamide hydrochloride, a piperidine opioid), Lomotil® (diphenoxylate hydrochloride with atropine sulfate, diphenoxylate being related to the narcotic meperidine), sold by G.D. Searle & Co., and Pepto-Bismol® (a bismuth subsalicylate composition) sold by Proctor and Gamble. However, although the opioids are described in Goodman and Gilmans *The Pharmacological Basis of Therapeutics,* Eighth Edition, Pergamon Press, New York, (1990) at pages 924–925 as being effective in treating moderate-to-severe diarrhea, it is cautioned that the opioids should not be used in patients with chronic ulcerative colitis or acute bacillary or amebic dysentery, since they appear to potentiate ulcerating processes in the colon and can provoke the development of toxic megacolon.

Many traditional remedies are said to have little or no value in the treatment of acute infectious diarrhea: these include kaolin, pectin, lactobacilli and muscarinic antagonists. Clonidine has also been said to be effective in the treatment of diabetic patients with watery diarrhea syndrome.

Substances available on the market provide balanced electrolytes to replace stool losses and provide maintenance requirements. Such products include Pedialyte® and Rehydralyte®, sold by Ross Laboratories and provide water, dextrose, potassium citrate, sodium chloride and sodium citrate. These compositions are expensive and rarely stocked in homes for immediate use when diarrhea begins. Therefore, clear liquids like ginger ale, colas, gelatin, tea, apple juice and chicken broth, none of which contains appropriate glucose or electrolyte concentrations, are used instead, possibly doing more harm than good. In any event, unlike the instant invention, the foregoing pharmaceuticals are not relatively inexpensive natural substances that have proven to be extremely effective in eliminating the symptoms of diarrhea.

SUMMARY OF THE INVENTION

The present invention provides a product which is active in the treatment of diarrhea in humans, including children and infants, as well as in warm-blooded animals generally, including dogs, horses and birds. Furthermore, the claimed composition does not have the disadvantages exhibited by products now on the market.

The invention at hand involves a composition comprising carrots, rice and glucose prepared in the manner disclosed subsequently. The composition may also include one or more of bananas, pineapple, soy beans and apples. Generally, the formulations employed to treat diarrhea comprise about 40 to about 60% by weight dried carrots, about 10 to about 25% by weight dried, cooked rice, and about 7 to about 15% by weight glucose. Additionally, 0.5 gram of maltodextrin is included in each formulation to bind the composition together. However, although the foregoing amounts have been shown to provide desirable results, the most important consideration is the effectiveness of the composition. It is expected that slightly more or less of one component may be employed relative to another without significantly changing the results reported.

The additional presence of bananas, pineapple, soy beans and/or apples, has been found to enhance the activity of the composition, in addition to making the agent more palatable to the patient. Because of the acidity in pineapple, the percentage weight of this component is maintained at a relatively low value, as shown in the examples. On the other hand, while soy beans are found to be helpful, because of their fiber, the taste of the soy beans is not universally popular. It is this property that determines the amount of soy bean employed. The weight of the apples present in any particular formulation would usually approximate that of the bananas. However, it is important that each of the components, as indicated below, be cooked, then dried and ground to a fine powder before being administered to a patient for the treatment of diarrhea.

DETAILED DESCRIPTION OF THE INVENTION

The materials for formulating the anti-diarrheal composition are prepared as follows:

Carrots—These are cleaned, sliced and placed in water, without salt, until the water reaches the boiling point. They are cooked for about 10–15 minutes until soft and are then strained and put into a food dehydrator. The carrots are vacuum dehydrated with a minimum of heat. This may take 24 hours to obtain a completely dry product. The dried carrots are thereafter ground to a fine powder. However, it has been observed that said powder has a gritty feel to it when rubbed with the fingers.

Rice Cereal—This ingredient is used in the form obtained as a commercial preparation, i.e., Gerbers® rice cereal. It is dehydrated, if not already adequately dried, and then ground. When the rice is in the form of a powder, it is added to the carrots and dry blended.

Bananas—Yellow bananas are sliced, dehydrated in a vacuum dehydrator and ground to a powder. The fruit is dry blended with the other components of the composition.

Pineapple—The fruit is very thinly sliced and then placed into a vacuum dehydrator, where water is removed. The dried pineapple is ground to a powder and added to the other components. Because pineapples have a very sharp acidic taste, the amount of pineapple, by weight, is limited to about 5 grams per batch of composition containing about 70 to 120 grams of material.

Soy beans—These are prepared with the capsule left on. The soy beans are cooked until soft, then dried and ground. Babies appear to dislike the taste. While natural flavors have been added to mask the taste, said flavors usually have excessive sugar and cause problems, in themselves. To avoid the problems, bananas are added instead of the separated natural flavors and glucose is used for sweetness. Of course, other readily digestible sugars may be employed instead of glucose, but might be more expensive.

Apples—These can be used up to about 15 grams, to improve the composition's flavor. The apples are sliced, cooked like carrots and then dehydrated in the vacuum dehydrator. Applesauce is not used because it exacerbates the diarrhea.

To prepare the composition, a "Gloria Bean Coffee Grinder" was used. As previously mentioned, everything was ground to a fine powder. The carrots, as already noted, tended to be a little gritty. However, even with the carrots, most of it becomes a fine powder. The composition containing a vegetable, a grain and a fruit, including the carrots and rice, has been found particularly beneficial.

ADMINISTRATION

The powdered composition can be administered to an infant as an addition to a formula, with a flat soda, like a cola or ginger ale, or with plain non-fat yogurt. Plain yogurt, although a dairy product, used in small amounts, with the formulation, is effective in controlling diarrhea in infants. However, there is no real restriction on how the formulation is given to the patient. If a distasteful carrier or component is avoided, the patient will more likely ingest the composition. It is critical to the effectiveness of the invention that the patient swallow the composition.

Although the composition has been used primarily to control diarrhea in infants, young children and adults, it has also been used for the same purpose with animals. Newborn horses sometimes develop diarrhea within nine days of birth. Previously, they have been administered Pepto-Bismol® in relatively large quantities. On the other hand, two doses of the instant product (4 tablespoons for the first dose and a lesser amount for the second dose) stop the diarrhea in the newborn horse. In medicating a young foal, two tablespoons of the composition were mixed with warm water and given with a bottle. However, because the horse refused to swallow the composition, the product was mixed with mare's milk and given through a tube into the horse's stomach. This stopped the diarrhea.

A dog was likewise treated with the present product with similar results. The product stopped the diarrhea.

A parrot suffering from diarrhea was given a little bit of the formulation with some food. The same type of results were obtained wherein the diarrhea was alleviated.

Several different formulations have been found to be effective in stopping diarrhea and to be readily accepted by patients. These products are described in the following examples:

EXAMPLE 1

The listed ingredients were prepared as previously described and were formulated into a composition in the amounts indicated.

| Carrots | 40 grams |
|---|---|
| Rice cereal | 10 grams |
| Bananas | 15 grams |
| Pineapple | 5 grams |
| Glucose | 10 grams |
| Maltodextrin | ½ gram |

EXAMPLE 2

| Carrots | 40 grams |
|---|---|
| Rice cereal | 10 grams |
| Bananas | 15 grams |
| Glucose | 5 grams |
| Maltodextrin | ½ gram |

EXAMPLE 3

| Carrots | 40 grams |
|---|---|
| Rice cereal | 20 grams |
| Pineapple | 5 grams |
| Glucose | 10 grams |
| Maltodextrin | ½ gram |

EXAMPLE 4

| Carrots | 40 grams |
|---|---|
| Rice cereal | 20 grams |
| Soy beans | 15 grams |
| Glucose | 10 grams |
| Maltodextrin | ½ gram |

EXAMPLE 5

| Carrots | 40 grams |
|---|---|
| Rice cereal | 20 grams |
| Soy beans | 5 grams |
| Bananas | 15 grams |
| Pineapple | 5 grams |
| Glucose | 10 grams |
| Apple | 15 grams |
| Maltodextrin | ½ gram |

EXAMPLE 6

| Carrots | 40 grams |
|---|---|
| Rice cereal | 20 grams |
| Soy beans | 5 grams |
| Bananas | 15 grams |
| Glucose | 10 grams |
| Maltodextrin | ½ gram |

EXAMPLE 7

| Carrots | 40 grams |
|---|---|
| Rice cereal | 20 grams |
| Soy beans | 5 grams |
| Pineapple | 5 grams |
| Glucose | 10 grams |
| Maltodextrin | ½ gram |

In addition, apple can be substituted for banana and pineapple may be used in small amounts in each of the formulations.

DOSAGE

Since the composition is composed of all natural products, there is no question of toxicity to the patient. In humans, the dosage depends upon the age of the patient. Infants are fed ½ teaspoon of the formulation with fluid, while children, adults and large animals are administered proportionately more, as shown below:

Dosages in humans, administered three times daily:

| Age | Amount |
|---|---|
| 0–3 months | half teaspoon |
| 3–6 months | 1 teaspoon |
| 6–12 months | 1½ teaspoon |
| 1–2 years | 2 teaspoon |
| 2–6 years | 1 tablespoon |
| 6–12 years | 1 to 1½ tablespoon |
| greater than 12 years | 2 tablespoon |

The powder is given to a patient experiencing a loose bowel movement.

Veterinary dosages depend to a great extent on the animal's size. Where the animal is under ten pounds, one half teaspoon of the composition is administered. In larger animals, the dosage depends on the size and severity of the condition.

The form of the composition is not limited to a powder. It may also be given as a capsule or as a tablet. The capsules include any form of conventional capsules, such as those made of gelatin, and the tablets are those conventionally used in the pharmaceutical field. The tablets may be chewing tablets or other types that the patient is found to prefer. Also, the powder may be placed in a compatible liquid and offered for sale or administration in this form. The powder, if kept in a freezer, will maintain its effectiveness over a long period of time. Powder placed in a freezer for almost a year was still effective in treating a case of diarrhea.

When the composition is administered to a patient, it cures the symptoms of diarrhea, which usually do not recur. The mechanism whereby this takes place is not understood, but it has been documented by patients who have been so treated. The same phenomenon, i.e., the non-recurrence of symptoms, is not experienced in all animals. Because it could not be determined whether the specific size of the powder particles contributed to the activity of the composition, the particles were measured and found to have a particle size distribution as shown below.

| Example No. | Nominal mean particle size (μm) | Mesh size | Amount retained or passed through (%) |
|---|---|---|---|
| 1 | 148 | ≧60 | 25.27 |
|  |  | ≦270 | 26.13 |
| 2 | 178 | ≧60 | 30.29 |
|  |  | ≦270 | 22.30 |
| 3 | 149 | ≧60 | 25.12 |
|  |  | ≦270 | 25.58 |
| 4 | 168 | ≧60 | 23.4 |
|  |  | ≦270 | 16.26 |
| 5 | 131 | ≧60 | 17.95 |
|  |  | ≦270 | 24.81 |
| 6 | 162 | ≧60 | 22.45 |
|  |  | ≦270 | 16.04 |
| 7 | 182 | ≧60 | 24.8 |
|  |  | ≦270 | 15.41 |

The nominal mean particle size was determined from the sieve analysis data by using the Sigmaplot for Windows (version 2.0).

From the foregoing data, it is apparent that the size of the powder particles is between 131 and 182 microns, the average being about 160 microns.

Notwithstanding the compositions' freedom from toxic effects, it is not prescribed for patients experiencing very high fever, lethargy and bloody diarrhea. These symptoms are indicative of bacterial diarrhea, as well as bacteremia and sepsis, thus raising a suspicion of other severe systemic disorders. However, in the usual case of diarrhea, as previously described, the composition is quite effective and its use is free from adverse effects.

Only the preferred embodiment of the invention and but a few examples of its versatility are shown and described in the present disclosure. It is to be understood that the invention is not only capable of use in various other combinations and environments, but also of changes or modifications within the scope of the inventive concept as expressed herein.

I claim:

1. A therapeutic composition for the treatment of diarrhea comprising carrots, rice, bananas and glucose in powdered form, the carrots and rice having been cooked and dried prior to being ground to a powder.

2. The composition of claim 1 also including pineapple in a dried and powdered form.

3. The composition of claim 2 also including soy beans in a dried and powdered form.

4. The composition of claim 3 also including apples in a dried and powdered form.

5. The composition of claim 1 also including soy beans in a dried and powdered form.

6. The composition of claim 1 also including apples in a dried and powdered form.

7. The composition of claim 1, wherein the carrots are present in a range of about 40 to about 60% by weight based on the entire composition.

8. The composition of claim 1 wherein maltodextrin is also present, in an amount of about 0.5 grams based upon a combined weight of the other components in the range of about 70 to about 120 grams.

9. The composition as in claim 1 comprising said carrots, rice, bananas and glucose in the following amounts:

40 g carrots;

10 g rice;

10 g glucose;

15 g bananas;

and further comprising maltodextrin and dried and powdered pineapple in the following amounts:

5 g pineapple; and 0.5 g maltodextrin.

10. The composition as in claim 1 comprising said carrots, rice, bananas and glucose in the following amounts:

40 g carrots;

10 g rice;

5 g glucose;

15 g bananas;

and further comprising 0.5 g maltodextrin.

11. The composition as in claim 1 comprising said carrots, rice, bananas and glucose in the following amounts:

40 g carrots;

20 g rice;

10 g glucose;

15 g bananas;

and further comprising maltodextrin and dried and powdered pineapple, soy beans and apples in the following amounts:

5 g pineapple;

5 g soy beans;

15 g apples; and 0.5 g maltodextrin.

12. The composition as in claim 1 comprising said carrots, rice, bananas and glucose in the following amounts:

40 g carrots;

20 g rice;

10 g glucose;

15 g bananas;

and further comprising maltodextrin and dried and powdered soy beans in the following amounts:

5 g soy beans; and 0.5 g maltodextrin.

13. A process for preparing a therapeutic composition as recited in claim 1 wherein carrots are cleaned, sliced and boiled in water until tender; then vacuum dried with minimal heat; and ground into a fine powder;

rice cereal is vacuum dried with minimal heat, like the carrots, and ground to a fine powder;

bananas are dried and ground into a fine powder; and the carrots, rice, bananas and glucose are mixed together and further ground to a fine powder.

14. A method for treating and alleviating diarrhea by administering to a patient suffering from diarrhea a therapeutically effective dose of a composition as defined in claim 1.

15. A method as set forth in claim 14 wherein the composition also includes pineapple in a dried and powdered form.

16. A method as set forth in claim 14 wherein the composition also includes soy beans in a dried and powdered form.

17. A method as set forth in claim 14 wherein the composition also includes apples in a dried and powdered form.

18. A method as set forth in claim 14 wherein the composition is administered in a carrier selected from the group consisting of a sweetened aqueous drink and non-fat yogurt.

19. A method as set forth in claim 14 wherein the composition is administered mixed with food.

20. A method as set forth in claim 14 herein the composition is administered mixed with mother's milk.

21. A method as set forth in claim 14 wherein the patient is a human being.

22. A method as set forth in claim 21 wherein the patient is an infant.

23. A method as set forth in claim 21 wherein the patient is a child.

24. A method as set forth in claim 21 wherein the patient is an adult.

25. A method as set forth in claim 14 wherein the patient is a warm blooded animal.

26. A method as set forth in claim 25 wherein the animal is a horse.

27. A method as set forth in claim 25 wherein the animal is a dog.

28. A method as set forth in claim 25 wherein the animal is a parrot.

29. A method as set forth in claim 14 wherein the composition is administered in a form selected from the group consisting of powders, capsules and tablets.

30. A composition for the treatment of diarrhea comprising carrots, rice and glucose in powdered form, the carrots and rice having been cooked and dried prior to being ground to a powder, said composition also containing at least one additional component selected from the group consisting of pineapple, soy beans and apples in dried and powdered form.

31. The composition of claim 30 wherein the additional component is pineapple in dried and powdered form.

32. The composition of claim 30 wherein the additional component is soy beans in dried and powdered form.

33. The composition of claim 30 wherein the additional component is apples in dried and powdered form.

* * * * *